(12) United States Patent
Voigtländer et al.

(10) Patent No.: US 8,329,925 B2
(45) Date of Patent: Dec. 11, 2012

(54) PROCESS FOR PREPARING SUBSTITUTED 1-O-ACYL-2-DEOXY-2-FLUORO-4-THIO-BETA-D-ARABINOFURANOSES

(75) Inventors: David Voigtländer, West Layfayette, IN (US); Michael Sander, Rösrath (DE); Michael Harre, Berliln (DE)

(73) Assignee: Libramedicina, Inc., Tokyo (JP)

( * ) Notice: Subject to any disclaimer, the term of this patent is extended or adjusted under 35 U.S.C. 154(b) by 209 days.

(21) Appl. No.: 12/959,735

(22) Filed: Dec. 3, 2010

(65) Prior Publication Data

US 2011/0152542 A1 Jun. 23, 2011

(30) Foreign Application Priority Data

Dec. 18, 2009 (EP) .................................. EP09075563
May 20, 2010 (EP) .................................. EP10163406

(51) Int. Cl.
*C07D 333/28* (2006.01)
(52) U.S. Cl. .......................................................... 549/66
(58) Field of Classification Search ...................... 549/66
See application file for complete search history.

(56) References Cited

U.S. PATENT DOCUMENTS

| 4,803,272 | A | 2/1989 | Anton et al. | 544/277 |
| 6,103,707 | A | 8/2000 | Yamada et al. | 514/81 |
| 6,147,058 | A | 11/2000 | Yoshimura et al. | 514/49 |
| 6,448,415 | B1 | 9/2002 | Lee et al. | 549/306 |
| 2009/0069263 | A1 | 3/2009 | Damha et al. | 514/44 |

FOREIGN PATENT DOCUMENTS

| WO | WO 97/37993 | 10/1997 |
| WO | WO 97/38001 | 10/1997 |
| WO | WO 2007/068113 | 6/2007 |

OTHER PUBLICATIONS

Jeong, et al. (2003) "N6-Substituted D-4'-Thioadenosine-5'-methyluronamides: Potent and Selective Agonists at the Human A3 Adenosine Receptor.", J. Med. Chem., 46(18):3775-3777.
Komine, et al. (2008) "Synthesis and structure-activity relationship studies of highly potent novel oxazolidinone antibacterials.", J. Med. Chem., 51(20):6558-6562.
Vanhessche, et al. (1990) "L-Ribulose: A novel chiral pool compound.", Tetrahedron Letters, vol. 31(16):2337-2340.
Varela, et al. (1993) "First synthesis of aldopentono-1,4-thiolactones.", J. Org. Chem., 58(27):7860-7864.
Wang, et al. (1988) "Synthesis of 2'(S), 3'(R),5'-trihydroxypentyladenine." Tetrahedron Letters, vol. 29(10):1107-1110.
Yoshimura, et al. (1997) "A Novel Synthesis of 2'-Modified 2'-Deoxy-4'-thiocytidines from d-Glucose." J. Org. Chem., 62(10):3140-3152.
Partial European Search Report in EP10163406, dated Nov. 24, 2010.
D.C. Baker et al. (1972) "Large-scale preparation of D-allose: observations on the steroselectivity of the reduction of 1,2:5,6-di-*O*-isopropylidene-α-D-*ribo*-hexofuranos-3-ulose hydrate." Carbohydr. Res. 24:192-197.
S. Miura et al. (1998) "Antitumor activity of a novel orally effective nucleoside, 1-(2-deoxy-2-fluoro-4-thio-β-D-arabinofuranosyl)cytosine." Cancer Lett. 129:103-110.
S. Miura et al. (1999) "Comparison of 1-(2-deoxy-2-fluoro-4-thio-β-D-arabinofuranosyl)cytosine with gemcitabine in its antitumor activity." Cancer Lett. 144:177-182.
J.K. Watts et al. (2006) Synthesis and conformational analysis of 2'-fluoro-5-methyl-4'-thioarabinouridine (4'S-FMAU) J. Org. Chem. 71:921-925.
Y. Yoshimura et al. (1997) "A novel synthesis of 2'-Modified 2'-Deoxy-4'-thiocytidines from D-glucose." J. Org. Chem. 62:3140-3152.
Y. Yoshimura et al. (1998) "An alternative synthesis of antineoplastic nucleoside 4'-thioFAC." Nucleic Acids Symposium Series 39:11-12.
Y. Yoshimura et al. (1999) "An alternative synthesis of antineoplastic 4'-thiocytidine analogue 4'-thioFAC." Tetrahedron Lett. 40:1937-1940.
Y. Yoshimura et al. (1999) "An alternative synthesis of the antineoplastic nucleoside 4'-thioFAC and its application to the synthesis of 4'-thioFAG and 4'-thiocytarazid." J. Org. Chem. 64:7912-7920.
Y. Yoshimura et al. (1999) "Synthetic studies on 2'-substituted-4'-thiocytidine derivatives as antineoplastic agents." Nucleosides Nucleotides 18:815-820.
Y. Yoshimura et al. (2000) "Synthesis and biological activities of 2'-deoxy-2'-fluoro-4'-thioarabinofuranosylpyrimidine and—purine nucleosides." Bioorg. Med. Chem. 8:1545-1558.
D.A. Zajchowski et al. (2005) "Anti-tumor efficacy of the nucleoside analog 1-(2-deoxy-2-fluoro-4-thio-β-D-arabinofuranosyl) cytosine (4'-thio-FAC) in human pancreatic and ovarian tumor xenograft models." Int. J. Cancer 114:1002-1009.

*Primary Examiner* — Taofiq A Solola
(74) *Attorney, Agent, or Firm* — Harness, Dickey & Pierce, P.L.C.; J. Timothy Keane; Kisuk Lee

(57) ABSTRACT

The present invention relates to a process for preparing 1-O-acyl-2-deoxy-2-fluoro-4-thio-β-D-arabinofuranoses having formula I and intermediates thereof:

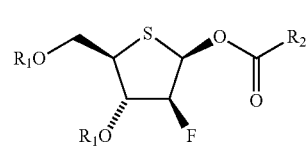

I wherein $R_1$ represents —C(O)—$C_1$-$C_6$-alkyl or —C(O)-aryl; and $R_2$ represents $C_1$-$C_6$-alkyl, $C_1$-$C_4$-perfluoroalkyl or aryl.

26 Claims, No Drawings

PROCESS FOR PREPARING SUBSTITUTED 1-O-ACYL-2-DEOXY-2-FLUORO-4-THIO-BETA-D-ARABINOFURANOSES

CROSS-REFERENCE TO RELATED APPLICATIONS

This application claims the benefit and priority to European Patent Application No. 09075563.8 filed on Dec. 18, 2009 and European Patent Application No. 10163406.1 filed on May 20, 2010. The entire disclosures of the applications identified in this paragraph are incorporated herein by reference.

FIELD

The present invention relates to a process for preparing 1-O-acyl-2-deoxy-2-fluoro-4-thio-β-D-arabinofuranoses and intermediates thereof.

BACKGROUND

4'-Thionucleosides are attractive compounds with respect to antiviral and antineoplastic activity. For example, 1-(2-deoxy-2-fluoro-4-thio-β-D-arabinofuranosyl)cytosine (4'-thio-FAC) was shown to have excellent antitumour activity in vitro and in vivo [Y. Yoshimura et al; *J. Org. Chem.* 1997, 62, 3140-3152; S. Miura et al, *Cancer Lett.* 1998, 129, 103-110; S. Miura et al, *Cancer Lett.* 1999, 144, 177-182; Y. Yoshimura et al, *Bioorg. Med. Chem.* 2000, 8, 1545-1558; D. A. Zajchowski et al, *Int. J. Cancer* 2005, 114, 1002-1009].

The invention relates in particular to a novel process for preparing compounds of formula I

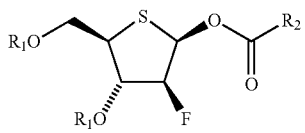

in which $R_1$ represents —C(O)—$C_1$-$C_6$-alkyl or —C(O)-aryl; and $R_2$ represents $C_1$-$C_6$-alkyl, $C_1$-$C_4$-perfluoroalkyl or aryl.

The compounds of the general formula I are key intermediates in the preparation of 4'-thionucleosides.

1-(2-Deoxy-2-fluoro-4-thio-β-D-arabinofuranosyl)cytosine[4'-thio-FAC]:

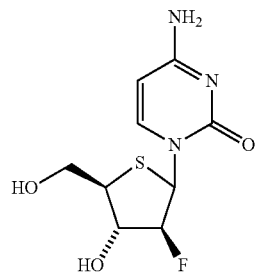

There is a particular interest in the preparation of 1-(2-deoxy-2-fluoro-4-thio-β-D-arabinofuranosyl)cytosine (4'-thio-FAC) with a view to the compound II:

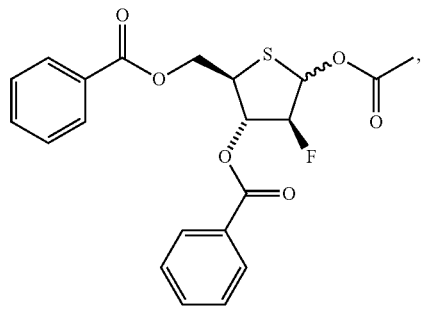

where in the text below the α-diastereomer of the anomeric acetate is referred to as IIα and IIβ is used for the β-isomer.

This compound and its preparation was described for the first time in WO 97/73993, WO 97/038001 and in the literature associated therewith [Y. Yoshimura et al, *J. Org. Chem.* 1999, 64, 7912-7920; Y. Yoshimura et al, *Nucleosides Nucleotides* 1999, 18, 815-820; Y. Yoshimura et al, *Nucleic Acids Symposium Series* 1998, 39, 11-12; Y. Yoshimura et al, *Tetrahedron Lett.* 1999, 40, 1937-1940].

In this context, a preparation route to compounds of the formula III is described

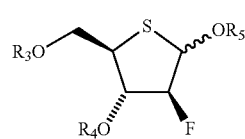

in which $R_3$ and $R_4$ represent alkyl, silyl or acyl, and $R_5$ represents acyl (Scheme 1).

[Scheme 1]

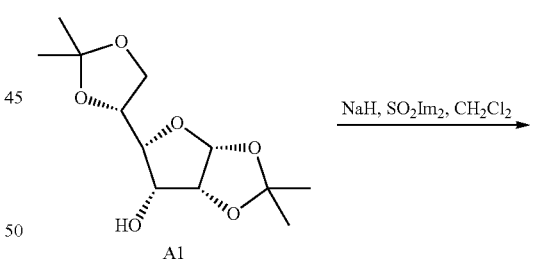

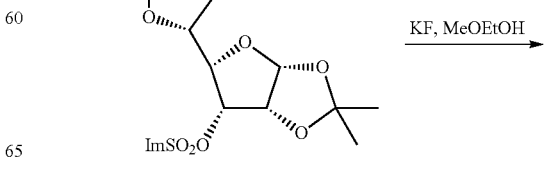

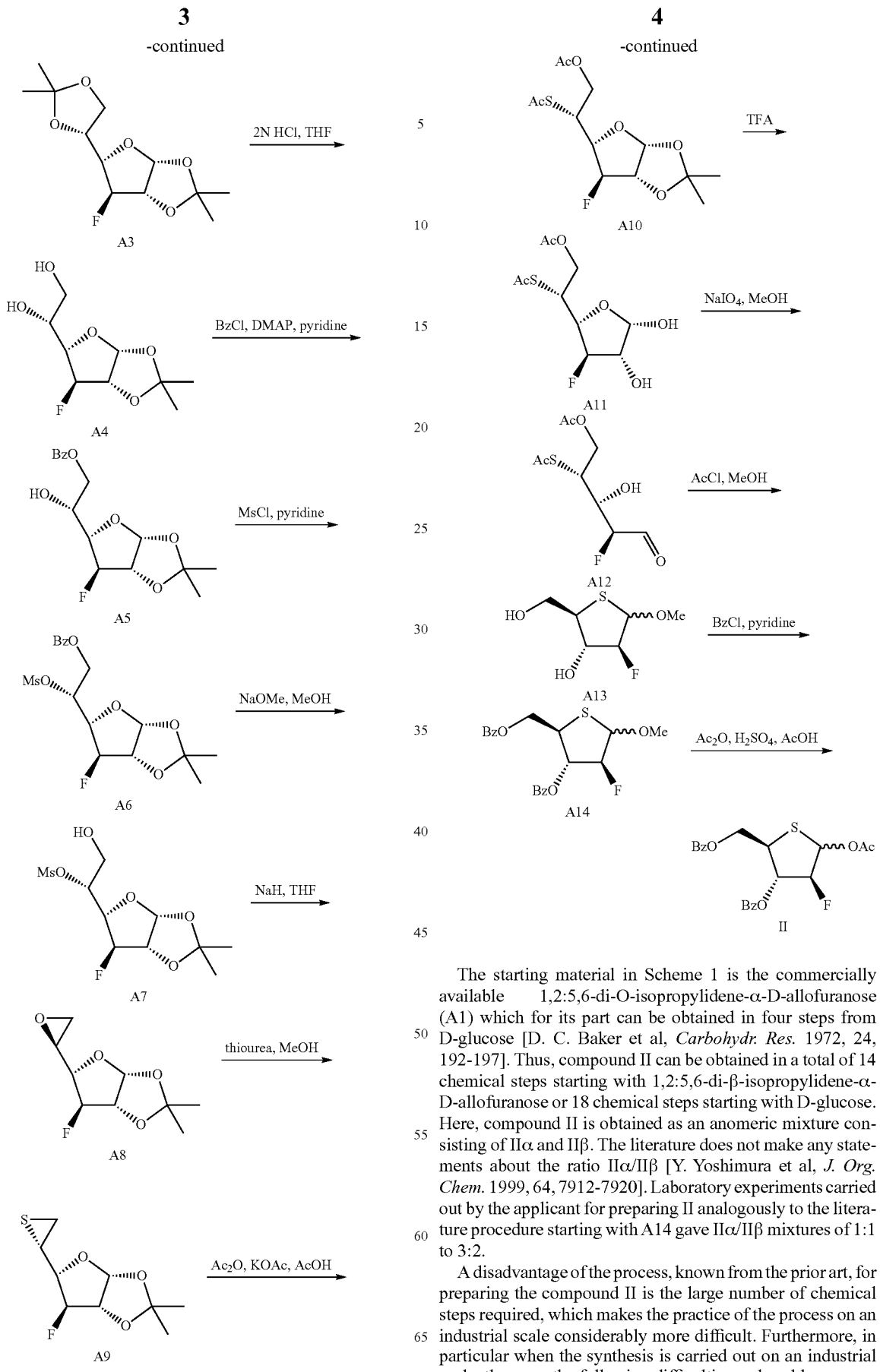

The starting material in Scheme 1 is the commercially available 1,2:5,6-di-O-isopropylidene-α-D-allofuranose (A1) which for its part can be obtained in four steps from D-glucose [D. C. Baker et al, *Carbohydr. Res.* 1972, 24, 192-197]. Thus, compound II can be obtained in a total of 14 chemical steps starting with 1,2:5,6-di-β-isopropylidene-α-D-allofuranose or 18 chemical steps starting with D-glucose. Here, compound II is obtained as an anomeric mixture consisting of IIα and IIβ. The literature does not make any statements about the ratio IIα/IIβ [Y. Yoshimura et al, *J. Org. Chem.* 1999, 64, 7912-7920]. Laboratory experiments carried out by the applicant for preparing II analogously to the literature procedure starting with A14 gave IIα/IIβ mixtures of 1:1 to 3:2.

A disadvantage of the process, known from the prior art, for preparing the compound II is the large number of chemical steps required, which makes the practice of the process on an industrial scale considerably more difficult. Furthermore, in particular when the synthesis is carried out on an industrial scale, there are the following difficulties and problems:

The process comprises at least five preparative chromatographic separations (prep-HPLC).

The intermediates A6, A7, A9, A12 are unstable.

Handling of the viscous liquids in stages A2, A3, A4, A8, A9, A11, A12 is difficult.

The compound A6 dissolves only very slowly in methanol. In the presence of sodium methoxide (NaOMe), a nucleophilic substitution of the mesylate group by a methoxy group in the compound A7 takes place as a side-reaction. Formation of by-product takes place in particular when the reaction is carried out on a relatively large scale.

After cleavage of the isopropylidene group, trifluoroacetic acid (TFA) has to be distilled off under reduced pressure since other alternatives for work-up result in a large formation of side-product. On an industrial scale, this is associated with considerable difficulties.

Owing to the long synthesis sequence and the fact that some of its steps cannot be scaled up, or only with considerable expense, the process shown in Scheme 1 is not suitable for the industrial commercial preparation of the compound II.

An alternative for preparing the compound II is described in WO 2007/068113 and the literature associated therewith [J. K. Watts et al, *J. Org. Chem.* 2006, 71, 921-925] and is summarized here in Scheme 2.

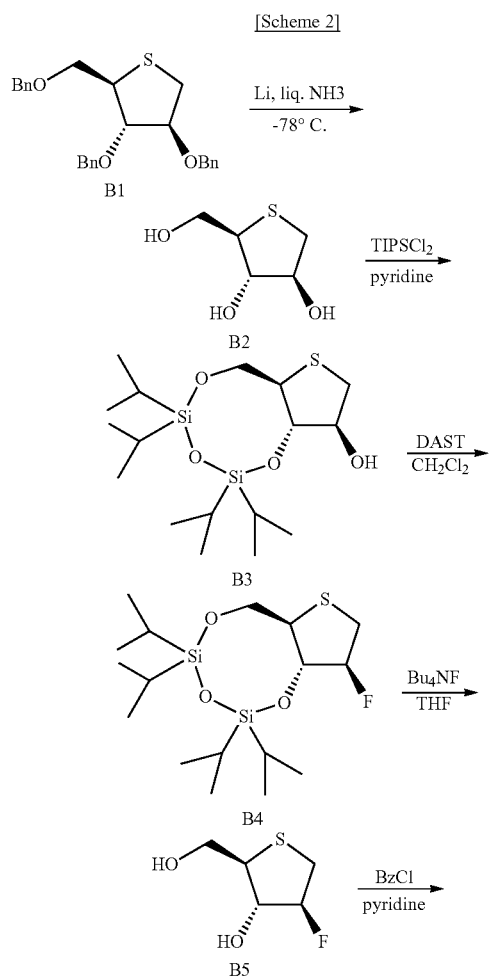

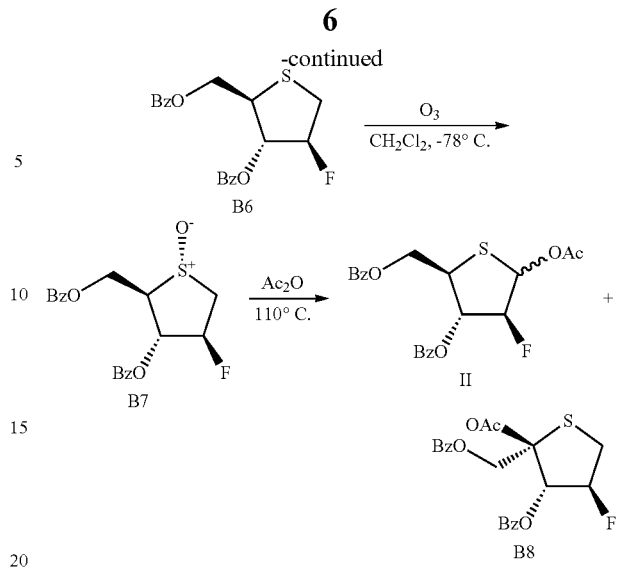

Here, in the last synthesis step, a mixture of the anomeric acetates II in a ratio IIα/IIβ of from 1:2 to 1:14 is obtained [see also J. K. Watts et al, *J. Org. Chem.* 2006, 71, 921-925]. The by-product B8 is removed by column chromatography.

Compound B1 can be prepared in 6 steps from L-xylose (which does not occur in nature) [J. K. Watts et al, *J. Org. Chem.* 2006, 71, 921-925]. Thus, compound II can be prepared in a total of 13 chemical steps from L-lyxose.

A particular disadvantage of this synthesis alternative is due to the fact that the starting material L-lyxose is expensive and very little is commercially available for a synthesis on an industrial scale.

Furthermore, in particular when the synthesis is carried out on an industrial scale, there are the following difficulties and problems:

On each synthesis stage, complicated protective group transformations and in each case a chromatographic purification have to be carried out.

The use of liquid ammonia and elemental lithium at very low temperatures (step B2).

Introduction and removal of a particular silyl protective group which has a high molar mass and is difficult to obtain commercially (steps B3 and B5).

Use of DAST as fluorinating agent. In addition to the fact that DAST is difficult to obtain, safety concerns (handling temperature, decomposition of DAST in an exothermal reaction with formation of gas) play an important role in the scale-up of this reaction (step 4).

The use of ozone at very low temperatures (B7).

High temperatures (110° C.) during the Pummerer rearrangement and the formation of about 20% of by-product B8 [J. K. Watts et al, *J. Org. Chem.* 2006, 71, 921-925].

Owing to the difficulties, described here, in the individual steps of the synthesis, which render scale-up difficult or impossible, and owing to the limited availability of the starting material, the process shown in Scheme 2 is likewise not very suitable for the industrial commercial preparation of the compound II.

SUMMARY

Against this background, it was the object of the present invention to provide an alternative process allowing the industrial preparation of compounds of formula I.

According to the invention, this object was achieved by a process which affords compounds of formula I in high yields in 10 chemical steps starting with commercially readily available compounds of formula IV via the key steps "introduction of the fluorine atom via targeted opening of a cyclic sulphate" and "Pummerer rearrangement of a sulphoxide using a special catalyst" (Scheme 3).

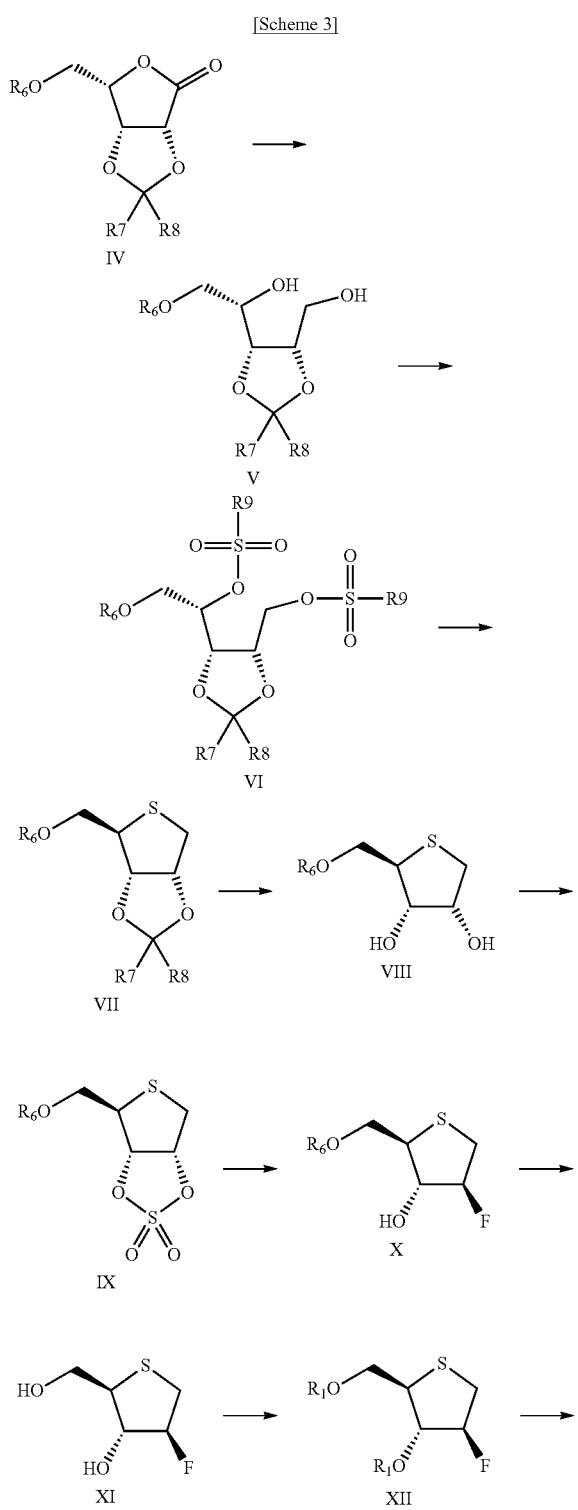

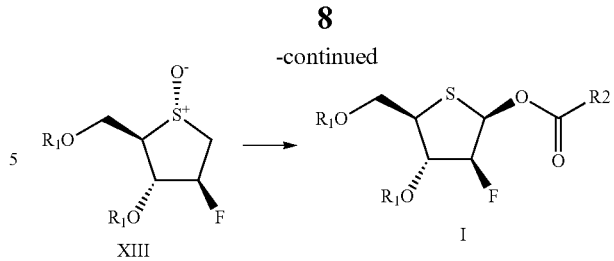

Compounds of formula IV, used as starting materials for the process according to the invention, can be synthesized in 4 chemical steps from natural and thus readily available D-ribose. Both D-ribose and compounds of the type IV (for example 5-O-benzyl-2,3-O-isopropylidene-L-lyxono-1,4-lactone) are commercially available (U.S. Pat. No. 6,448,415 B1).

Furthermore, the process according to the invention uses exclusively reagents which are readily available even in kg amounts.

The intermediates V, VI and VII are isolated only as crude products and in each case employed directly for the next step. Finally, the compound VIII is crystallized in high purity (>97%). Thus, time- and resource-intensive purifications (for example preparative chromatography) can be dispensed with.

Steps IX, XI and XII are likewise not isolated and directly used as crude materials for the subsequent step.

According to the invention, over the entire synthesis sequence, only 3 intermediates (VIII, X and XIII) have to be isolated, and only a single preparative chromatography is required (X). The intermediates VIII, XII and the product I (II) are isolated in high yields and high purities (>93%) by crystallization.

The process according to the invention does not require any complicated protective group transformations.

The oxidation of the sulphide XII can be carried out in a targeted manner at room temperature using OXONE (potassium monopersulphate triple salt, 2 $KHSO_5 \cdot KHSO_4 \cdot K_2SO_4$), overoxidation can be excluded without any problems by using equimolar amounts (cf. Scheme 2, reaction yielding B7).

According to the invention, the Pummerer rearrangement (XIII→I) is carried out in the presence of catalytic amounts of potassium bisulphate. By using this catalyst, it is possible to achieve high yields (>80%) and at the same time very little side-product formation (<5%) at low reaction temperatures (<90° C.) [cf. Scheme 2, reaction yielding II]. The crude product I obtained comprises so few impurities and also only very small proportions of the α-anomer that a simple crystallization is sufficient for purification.

The process according to the invention does make use of general chemical transformations, known to the person skilled in the art, for constructing a thiofuranose via formation of a diol, its activation via a bissulphonate and cyclization with sodium sulphide; for protective group techniques and for oxidizing a sulphide with OXONE. However, a particular aspect of the present invention is the targeted and highly efficient construction of the individual stereocentres of the thiofuranoses.

A further aspect of the present invention is the stereospecific introduction of the fluorine atom at the C3 atom of compound X via stereoselective opening of the cyclic sulphate IX.

DETAILED DESCRIPTION

In the first step of the process according to the invention for preparing a compound of formula I:

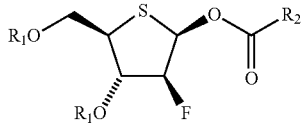

in which
$R_1$ represents —C(O)—$C_1$-$C_6$-alkyl or —C(O)-aryl; and
$R_2$ represents $C_1$-$C_6$-alkyl, $C_1$-$C_4$-perfluoroalkyl or aryl,
a lyxonolactone of formula IV:

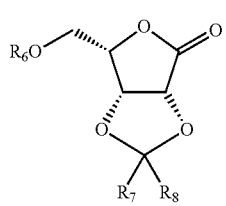

in which
$R_6$ represents $C_1$-$C_6$-alkyl or arylmethylene; and
$R_7$ and $R_8$ independently of one another represent hydrogen, $C_1$-$C_6$-alkyl, $C_1$-$C_4$-perfluoroalkyl or aryl;
is reduced in the presence of 0.5-10 molar equivalents of hydride donors of the formula A(AlH$_4$) or A(BH$_4$), in which A represents an alkali metal, to give the diol of formula V:

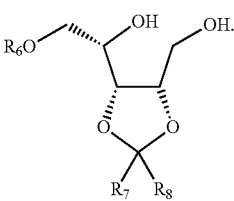

Here, preference is given to using 0.5-1.5 molar equivalents of lithium aluminium hydride (LiAlH$_4$). The reaction step is preferably carried out at a temperature between 0° C. and 30° C.

In the second step, the diol V is reacted with at least 2 molar equivalents of sulphonyl chloride $R_9$—SO$_2$Cl or sulphonic anhydride $R_9$—SO$_2$—O—SO$_2$—$R_9$, in which $R_9$ represents $C_1$-$C_6$-alkyl, $C_1$-$C_4$-perfluoroalkyl or aryl, preferably 2-5 molar equivalents of methanesulphonyl chloride, in the presence of at least 2 molar equivalents of a tertiary amine (for example trimethylamine, triethylamine, diisopropylethylamine) or a pyridine (for example pyridine, 4-N,N-dimethylaminopyridine, collidine, picolines, lutidines), preferably 2-5 molar equivalents of triethylamine, to give a compound of formula VI:

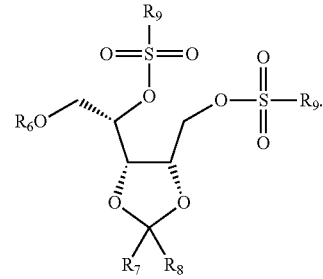

The reaction step is preferably carried out at a temperature between 0° C. and 30° C.

In the third step, the bissulphonate VI is reacted with at least 1 molar equivalent of sodium sulphide (Na$_2$S) in a polar aprotic solvent, such as, for example, DMF, NMP, DMA, DMSO, DMEU, preferably NMP (N-methylpyrrolidone), at a temperature of more than 50° C., preferably at temperatures between 50 and 100° C., to give the thiofuranose of formula VII:

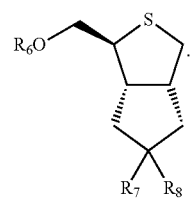

In step four, the thiofuranose of formula VII is converted in a solvent mixture of water and an organic solvent selected from the group of the ethers (for example diethyl ether, THF, dioxane, MTBE), alcohols (for example methanol, ethanol, isopropanol), carboxylic acids (for example acetic acid), aromatic hydrocarbons (for example benzene, toluene), preferably in a mixture of tetrahydrofuran (THF) and water, with 0.01-5 molar equivalents of an acid selected from the group of the mineral acids (for example HCl, H$_2$SO$_4$, H$_3$PO$_4$), alkanesulphonic acids (for example methanesulphonic acid), arylsulphonic acids (for example benzenesulphonic acid, toluenesulphonic acid), perfluorosulphonic acids (for example trifluoromethanesulphonic acid, nonafluorobutanesulphonic acid) or perfluoroalkanecarboxylic acids (for example trifluoroacetic acid), preferably 0.01-5 molar equivalents of H$_2$SO$_4$, into the diol of formula VIII:

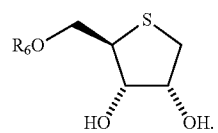

The reaction step is preferably carried out at a temperature between 20° C. and 100° C.

The diol VIII is isolated by crystallization from a solvent mixture of an alkane or mixtures thereof—preferably heptane—and a carboxylic ester—preferably isopropyl acetate or ethyl acetate.

In step five, the diol of general formula VIII is reacted in the presence of at least 0.2 molar equivalents of a base of the formula AH, A$_2$CO$_3$ or A(OtBu), in which A represents an alkali metal; preferably in the presence of 0.2-3 molar equivalents of sodium hydride, with 1-2 molar equivalents of a diol-activating reagent of the formula X$_1$—SO$_2$—X$_2$, in which X$_1$ and X$_2$ independently of one another represent Cl or imidazoyl, preferably with 1-2 molar equivalents of sulphonyldiimidazole, to give the cyclic sulphate ester of formula IX:

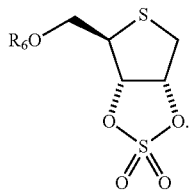

IX

The reaction step is preferably carried out at a temperature between −5° C. and 20° C.

In step six, the cyclic sulphate ester of formula IX is initially reacted with 1-3 molar equivalents of an ammonium fluoride of the formula N(R$_{11}$)$_4$F, in which R$_{11}$ represents C$_1$-C$_6$-alkyl, preferably with 1-3 molar equivalents of tetrabutylammonium fluoride, at a temperature between 0° C. and 30° C., and the reaction mixture obtained in this manner is reacted with an acid selected from the group of the mineral acids (for example HCl, H$_2$SO$_4$), alkylsulphonic acids (for example methanesulphonic acid), arylsulphonic acids (for example benzenesulphonic acid, toluenesulphonic acid), perfluorosulphonic acids (for example trifluoromethanesulphonic acid, nonafluorobutanesulphonic acid) or perfluoroalkanecarboxylic acids (for example trifluoroacetic acid), preferably with sulphuric acid (H$_2$SO$_4$), to give the ether of formula X:

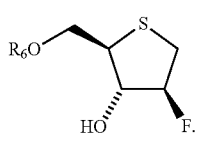

X

The second partial step of the reaction is preferably carried out at a temperature between 20° C. and 70° C.

In step seven, the ether of the formula X is initially, in partial step a), reacted in the presence of at least 1 molar equivalent of a boron halide BY$_3$, in which Y represents F, Cl or Br, preferably using 1-4 molar equivalents of boron trichloride, at a temperature between 0° C. and −80° C.

In partial step b), the reaction mixture obtained in partial step a) is reacted with a mixture of an alcohol component selected from the group consisting of a C$_1$-C$_6$-alkanol (for example methanol, ethanol, n-propanol, isopropanol, n-butanol, t-butanol, isobutanol), an arylalkanol (for example benzyl alcohol) and phenols (for example phenol); and a base selected from the group of aliphatic tertiary amines (for example trimethylamine, triethylamine, diisopropylethylamine) or from the group of pyridines (for example pyridine, 4-N,N-dimethylaminopyridine, collidine, picolines, lutidines); preferably using a mixture of methanol and pyridine, to give the diol of formula XI:

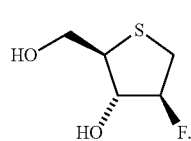

XI

The process and quenching of the reaction mixture are preferably carried out at temperatures between 0° C. and −80° C.

In step eight, the diol of formula XI is reacted in the presence of at least 2 molar equivalents of a base selected from the group of the aliphatic tertiary amines (for example trimethylamine, triethylamine, diisopropylethylamine) or from the group of the pyridines (for example pyridine, 4-N,N-dimethylaminopyridine, collidine, picolines, lutidines), preferably using 2-10 molar equivalents of pyridine, with at least 2 molar equivalents of an acid chloride R$_1$—Cl or an acid anhydride R$_1$—O—R$_1$, in which R$_1$ represents —C(O)—C$_1$-C$_6$-alkyl or —C(O)-aryl; preferably using 2-5 molar equivalents of benzoyl chloride, to give the compound of formula XII:

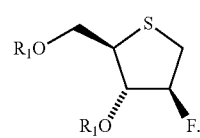

XII

In step nine, the sulphide of formula XII is oxidized in a solvent mixture of water and a ketone of the formula R$_9$—C(O)—R$_9$' in which R$_9$ and R$_9$' independently of one another represent C$_1$-C$_6$-alkyl, C$_1$-C$_4$-perfluoroalkyl or aryl, preferably acetone, with 0.5-1 molar equivalent of an alkali metal persulphate of the formula AHSO$_5$, in which A$^+$ represents an alkali metal, preferably using 0.5-1 molar equivalent of OXONE (potassium monopersulphate triple salt, 2 KHSO$_5$*KHSO$_4$*K$_2$SO$_4$), at a temperature between 0° C. and 50° C. to give the sulphoxide of formula XIII:

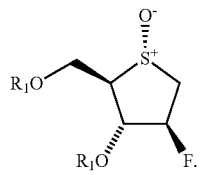

XIII

The product XIII is isolated by crystallization from a suitable solvent, preferably from methyl tert-butyl ether.

In step ten, the sulphoxide of formula XIII is reacted with at least 1 molar equivalent of an acid anhydride R$_2$—C(O)—O—C(O)$_2$, in which R$_2$ represents C$_1$-C$_6$-alkyl, C$_1$-C$_4$-perfluoroalkyl or aryl; preferably using at least 5 molar equivalents of acetic anhydride, in the presence of 0.01-2 molar equivalents of a protic acid selected from the group of the mineral acids (for example HCl, HBr, H$_2$SO$_4$, H$_3$PO$_4$, alkali metal bisulphates, monobasic alkali metal phosphates), alkanesulphonic acids (for example methanesulphonic acid), arylsulphonic acids (for example benzenesulphonic acid, toluenesulphonic acid), perfluorosulphonic acids (for example trifluoromethanesulphonic acid, nonafluorobutanesulphonic acid) or perfluoroalkanecarboxylic acids (for example trifluoroacetic acid), or in the presence of 0.01-2 molar equivalents of a Lewis acid (for example LiCl, MgBr$_2$, Ti(OR$_{13}$)$_4$), in which R$_{13}$ represents C$_1$-C$_6$-alkyl or arylmethylene; preferably in the presence of 0.01-2 molar equivalents of potassium bisulphate; at a temperature between 30° C. and 100° C. to give the compound of formula I:

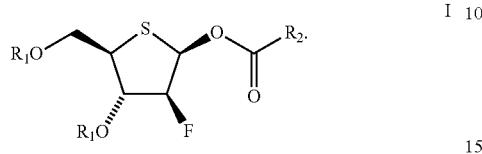

The product I is isolated by crystallization from a suitable solvent, preferably ethanol.

Hitherto, the literature does not provide any examples in which potassium bisulphate catalyses the Pummerer rearrangement of a sulphoxide to the corresponding thioacetal and prevents the formation of side-products.

The C$_1$-C$_6$-alkyl groups of the radicals R$_1$, R$_2$, R$_6$, R$_7$, R$_8$, R$_9$, R$_9$', R$_{11}$, and R$_{13}$ can, for example, be methyl, ethyl, n-propyl, isopropyl, n-butyl, isobutyl, sec-butyl, tert-butyl, n-pentyl or n-hexyl groups.

The arylmethylene groups of the radicals R$_6$, R$_9$, and R$_{13}$ can, for example, be benzyl or 4-methoxybenzyl groups.

The aryl groups of the radicals R$_1$, R$_2$, R$_7$, R$_8$, R$_9$, and R$_9$' can, for example, be phenyl or substituted phenyl groups.

The C$_1$-C$_4$-perfluoroalkyl groups of the radicals R$_2$, R$_7$, R$_8$, R$_9$, and R$_9$' can, for example, be trifluoromethyl, pentafluoroethyl or nonafluorobutyl groups.

The alkali metals A of the hydride donors of the formulae A(AlH$_4$), A(BH$_4$), of the bases AH, A$_2$CO$_3$, AOtBu, of the alkali metal persulphates AHSO$_5$ can, for example, be lithium, sodium or potassium.

The —C(O)—C$_1$-C$_6$-alkyl groups of the radical R$_1$ can, for example, be acetyl, n-propanoyl, isopropanoyl, n-butanoyl, t-butanoyl, isobutanoyl, n-pentanoyl, or n-hexanoyl groups.

The —C(O)-aryl groups of the radical R$_1$ can, for example, be benzoyl or substituted benzoyl groups.

Preferably, the process according to the invention is used for preparing the compound I (according to Scheme 3) in which R$_1$ represents benzoyl, and R$_2$ represents methyl, i.e. for preparing the compound of formula IIβ.

According to the present invention, particular preference is given to the process for preparing the compound of formula IIβ (according to Scheme 3) in which R$_7$, R$_8$ and R$_9$ represent methyl, and R$_6$ represents benzyl.

Furthermore, the present invention also relates to the intermediates of the preferred embodiment of the process according to the invention (Scheme 4), in particular 1-O-benzyl-3,4-O-isopropylidene-L-arabinitol (C2);

1-O-benzyl-3,4-O-isopropylidene-2,5-di-O-methanesulphonyl-L-arabinitol (C3);

1,4-anhydro-5-O-benzyl-2,3-O-isopropylidene-4-thio-D-ribitol (C4);

1,4-anhydro-5-O-benzyl-2,3-O-sulphonyl-4-thio-D-ribitol (C6);

1,4-anhydro-5-O-benzyl-2-deoxy-2-fluoro-4-thio-D-arabinitol (C7).

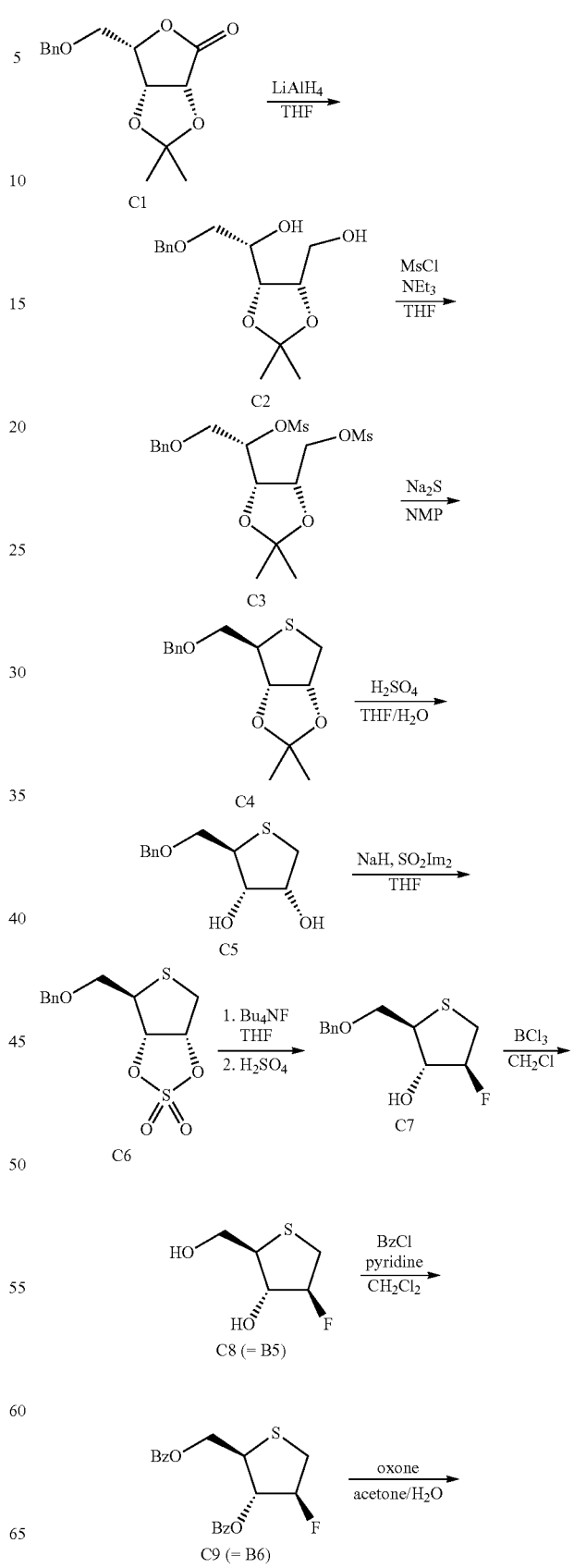

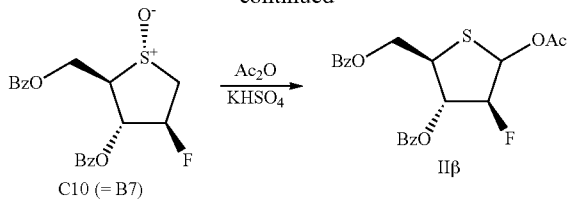

C10 (=B7) → IIβ

The compound C1 (5-O-benzyl-2,3-O-isopropylidene-L-lyxono-1,4-lactone) is commercially available. Hereinbelow, the procedures for the reactions shown in Scheme 4 are described.

Synthesis Procedures

1-O-Benzyl-3,4-O-isopropylidene-L-arabinitol (C2)

At 0-10° C., 44.68 g (116.78 mmol) of lithium aluminium hydride are metered into a solution of 50 g (179.66 mmol) of C1 in 450 ml of THF, and the mixture is stirred until the reaction has ended. At 20° C., water and aqueous sodium hydroxide solution are then added, and the precipitated solid is filtered off and washed product-free using THF. The solution of the crude product is concentrated and freed completely from the solvent. This gives 53.26 g of C2 (105%) as a crude product which is used in this form for the subsequent step C3.

$^1$H-NMR (400 MHz, DMSO): 7.39-7.24 (m, 5H, H-7 to H-9), 4.81 (t, 1H, 5.46 Hz, 1-OH), 4.65 (d, 1H, 5.84 Hz, 4-OH), 4.5 (s, 2H, 2×H-6), 4.15-4.00 (m, 2H, H-2 and H-3), 3.76 (qd, 1H, 6 Hz, 2.5 Hz, H-4), 3.7-3.55 (m, 2H, 2×H-1), 3.49-3.35 (m, 2H, 2×H-5), 1.38 (s, 3H, 10-CH$_3$), 1.25 (s, 3H, 10-CH3).

$^{13}$C-NMR (75 MHz, CDCl$_3$): 138.0, 128.8, 128.2, 128.1 (Ar), 108.9 (O—C—O), 77.7 (CH2), 76.9 (CH2), 73.8 (CH), 71.9 (CH), 68.9 (CH2), 61.0 (CH), 28.1 (CH3), 25.6 (CH3).

1-O-Benzyl-3,4-O-isopropylidene-2,5-di-O-methanesulphonyl-L-arabinitol (C3)

At 20° C., 54.54 g (538.97 mmol) of triethylamine are added to a solution of 53.26 g (179.66 mmol assuming a yield of 100% in step C2) of C2 (crude product) in 450 ml of THF, and 39.39 g (431.17 mmol) of methanesulphonyl chloride are metered in at 0-10° C. The mixture is then stirred until the reaction has ended, water is added and the phases are separated. The aqueous phase is extracted with MTBE, and the combined organic phases are washed with sat. sodium chloride solution and dilute sodium bicarbonate solution. The solution of the crude product is concentrated and freed completely from the solvents. This gives 86.66 g of C3 (110%) as a crude product which is used in this form for the subsequent step C4.

$^1$H-NMR (400 MHz, CDCl$_3$): 7.40-7.30 (m, 5H), 4.90 (dt, 1H, 11.5 Hz, 6.6 Hz), 4.56 (dd, 2H, 11.8 Hz), 4.42-4.39 (m, 2H), 4.38-4.35 (m, 2H), 3.83 (dd, 1H, 10.61 Hz, 6.06 Hz), 3.70 (dd, 1H, 10.61 Hz, 5.05 Hz), 3.10 (s, 3H), 3.02 (s, 3H), 1.50 (s, 3H), 1.37 (s, 3H).

$^{13}$C-NMR (75 MHz, CDCl$_3$): 136.8, 128.6, 128.2, 128.0 (Ar), 109.7 (O—C—O), 77.8. 75.6, 74.5, 73.7 (CH2), 69.6 (CH2), 67.7 (CH2), 39.0, 37.5, 27.2, 25.4.

1,4-Anhydro-5-O-benzyl-2,3-O-isopropylidene-4-thio-D-ribitol (C4)

50.99 g (215.59 mmol) of sodium sulphide (33% pure) are added to a solution of 86.66 g (179.66 mmol assuming a yield of 100% in step C3) of C3 (crude product) in 550 ml of N-methyl-2-pyrrolidone, and the mixture is heated to an internal temperature of 80° C. and stirred at this temperature until the reaction has ended. At an internal temperature of 20° C., water and MTBE are then added, the phases are separated and the aqueous phase is extracted with MTBE. The combined organic phases are finally washed with water. The solution of the crude product is concentrated and freed completely from the solvents. This gives 56.41 g of C4 (112%) as a crude product which is used in this form for the subsequent step C5.

$^1$H-NMR (400 MHz, DMSO): 7.40-7.25 (m, 5H, H-7 to H-9), 4.89 (t, 1H, 4.7 Hz, H-2), 4.73 (d, 1H, 5.65 Hz, H-3), 4.50 (s, 2H, 2×H-6), 3.55-3.42 (m, 2H, 2×H-5), 3.37 (t, 1H, 6.2 Hz, H-4), 3.10 (dd, 1H, 12.6 Hz, 4.7 Hz, H-1'), 2.76 (d, 1H, 12.6 Hz, H-1').

$^{13}$C-NMR (75 MHz, CDCl$_3$): 137.9, 128.4, 127.9, 127.5 (Ar), 110.9 (O—C—O), 86.3 (CH), 83.8 (CH), 73.2 (CH2), 72.2 (CH2), 53.3 (CH), 38.3 (CH2), 27.2 (CH3), 25.3 (CH3).

1,4-Anhydro-5-O-benzyl-4-thio-D-ribitol (C5)

A solution of 50 ml of water and 9.22 g (0.094 mmol) of sulphuric acid is added to the solution of 56.41 g (179.66 mmol assuming a yield of 100% in step C4) of C4 (crude product) in 450 ml of THF, and the mixture is heated to 70° C. and stirred at this temperature for a plurality of hours. To achieve complete conversion, a few ml are distilled off at 70° C. MTBE is then added at 20° C., the phases are separated and the aqueous phase is extracted with MTBE. The combined organic phases are neutralized with saturated potassium carbonate solution. The solid is filtered off and washed product-free using MTBE. The solution of the crude product is redistilled to isopropyl acetate, and the product is crystallized by addition of heptane. This gives 33.67 g (78% over 4 steps starting with C1) of C5.

$^1$H-NMR (400 MHz, CDCl$_3$): 7.39-7.29 (m, 5H), 4.56 (s, 2H), 4.37 (dt, 1H, 7.33 Hz, 3.54 Hz), 4.04 (dt, 1H, 7.07 Hz, 6.82 Hz), 3.70 (dd, 1H, 9.09 Hz, 5.31 Hz), 3.62 (t, 1H, 9.09 Hz), 3.56-3.51 (m, 1H), 3.11 (d, 1H, 3.54 Hz), 3.05 (dd, 1H, 11.62 Hz, 4.55 Hz), 2.85 (dd, 1H, 11.62 Hz, 3.03 Hz), 2.65 (d, 1H, 3.54 Hz).

$^{13}$C-NMR (75 MHz, CDCl$_3$): 137.4, 128.6, 128.0, 127.8 (Ar), 80.4, 74.8, 73.6 (CH2), 73.0 (CH2), 47.0, 33.6 (CH2). Melting point: 78-82° C.

1,4-Anhydro-5-O-benzyl-2,3-O-sulphonyl-4-thio-D-ribitol (C6)

At 0° C., a solution of 50 g (208.06 mmol) of C5 in 75 ml of THF is added to a suspension of 2.5 g of sodium hydride (in mineral oil) in 100 ml of THF, and the mixture is stirred at 0° C. for 1-2 hours. At 0° C., a solution of 45.36 g of sulphonyldiimidazole in 450 ml of THF is then metered in, and the mixture is stirred at 20° C. until the reaction is ended. In this form, the crude product is used directly for the subsequent step C7.

$^1$H-NMR (400 MHz, CDCl$_3$): 7.40-7.26 (m, 5H), 5.41 (dt, 1H, 6.06 Hz, 3.28 Hz), 5.33 (dd, 1H, 6.32 Hz, 2.78 Hz), 4.54 (d, 2H, 2.53 Hz), 3.81 (dd, 1H, 9.85 Hz, 4.29 Hz), 3.72 (m, 1H), 3.64 (dd, 1H, 9.85 Hz, 4.80 Hz), 3.47 (dd, 1H, 13.39 Hz, 5.81 Hz), 3.16 (dd, 1H, 13.39 Hz, 3.28 Hz).

$^{13}$C-NMR (75 MHz, CDCl$_3$): 137.0, 128.6, 128.2, 127.7 (Ar), 87.9, 86.1, 73.7 (CH2), 71.2 (CH2), 51.6, 36.8 (CH2).

1,4-Anhydro-5-O-benzyl-2-deoxy-2-fluoro-4-thio-D-arabinitol (C7)

At 20° C., a solution of 131.3 g of tetrabutylammonium fluoride trihydrate in 150 ml of THF is metered into the solution of the crude product from the preparation of compound C6. The mixture is stirred at 30° C. until the reaction is ended.

The reaction mixture is then adjusted to pH 1 using sulphuric acid (33% strength) and stirred at 50° C. until the reaction is ended. At 20° C., the pH is then adjusted to 7-10 using aqueous potassium hydroxide solution, and the precipitate formed is filtered off. The phases are separated and the aqueous phase is extracted with dichloromethane. The combined organic phases are concentrated and the crude product is, after complete removal of the solvent, purified by chromatography. This gives 22.68 g of C7 (45%).

$^1$H-NMR (400 MHz, CDCl$_3$): 7.4-7.27 (m, 5H, H-7 to H-9), 5.04 (qd, 1H, 51.7 Hz, 5.44 Hz, H-2), 4.55 (s, 2H, 2×H-6), 4.37 (td, 1H, 11.7 Hz, 4.9 Hz, H-3), 3.68-3.55 (m, 2H, 2×H-5), 3.45-3.38 (m, 1H, H-4), 3.2-2.99 (m, 2H, 2×H-1).

$^{13}$C-NMR (100 MHz, CDCl$_3$): 137.65, 128.52, 127.91, 127.77 (Ar), 97.27 (C-2), 79.10 (C-3), 73.46 (C-6), 72.69 (C-5), 48.58 (C-4), 31.72 (C-1).

$^{19}$F-NMR (376 MHz, CDCl$_3$): −183.14 (m, 2-F).

Melting point: 83-85° C.

1,4-Anhydro-2-deoxy-2-fluoro-4-thio-D-arabinitol (C8)

At a temperature of <−65° C., a solution, pre-cooled to −10° C., of 50 g (206.35 mmol) of C7 in 350 ml of dichloromethane is added to 546.82 g (412.69 mmol) of boron trichloride (1 mol/l in dichloromethane). After 30 minutes at <−65° C., the reaction is checked for complete conversion. A mixture of 150 ml of methanol and 116 ml of pyridine is then added at <−65° C. to the reaction mixture, and the mixture is heated to 20° C. after 15 minutes. The solvents are removed completely by distillation under reduced pressure. Dichloromethane is then added to the residue, and the solvent is removed completely. This gives 133 g of C8 (423%) as a crude product (contains residual amounts of pyridine and pyridinium hydrochloride) which is used in this form for the subsequent step C9.

$^1$H-NMR (400 MHz, DMSO): 5.49 (d, 1H, 4.77 Hz, 3-OH), 4.98 (qd, 1H, 51.55 Hz, 3.76 Hz, H-2), 4.94 (t, 1H, 5.2 Hz, 5-OH), 4.17 (ddd, 1H, 15.18 Hz, 4.14 Hz, 3.76 Hz H-3), 3.61-3.53 (m, 1H, H-5), 3.37-3.30 (m, 1H, H-5'), 3.19-3.02 (m, 2H, H-4 and H-1), 2.93 (ddd, 1H, 18.22 Hz, 12.1 Hz, 3.76 Hz, H-1').

$^{13}$C-NMR (75 MHz, CDCl$_3$): 97.1 (d, 185 Hz, C-2), 77.5 (d, 24 Hz, C-3), 63.3 (d, 3 Hz, C-5), 50.9 (d, 4 Hz, C-4), 31.1 (d, 22 Hz, C-1).

1,4-Anhydro-2-deoxy-2-fluoro-3,5-di-O-benzoyl-4-thio-D-arabinitol (C9)

133 g (206.35 mmol assuming a yield of 100% in step C8) of C8 (crude product) are dissolved in 400 ml of dichloromethane, and 97.92 g (1237.9 mmol) of pyridine are added. 87.01 g (618.97 mmol) of benzoyl chloride are then added dropwise at 10° C., and the mixture is stirred at 20° C. until the reaction has ended. Methanol is then added, and the mixture is stirred for 1 hour. Finally, water is added and the phases are separated. The solution of the crude product is concentrated and freed completely from the solvent. This gives 114.53 g of C9 (154%) as a crude product which is used in this form for the subsequent step C10.

$^1$H-NMR (400 MHz, CDCl$_3$): 8.20-8.00 (m, 4H), 7.65-6.90 (m, 6H), 5.85 (dt, 1H, 9.98 Hz, 2.64 Hz), 5.40 (ddd, 1H, 48.79 Hz, 7.16 Hz, 3.01 Hz), 4.54 (s, 1H), 4.51 (s, 1H), 3.95-3.82 (m, 1H), 3.45-3.35 (m, 1H), 3.35-3.28 (m, 1H).

$^{13}$C-NMR (75 MHz, CDCl$_3$): 165.0 (C=O), 133.6, 133.1, 129.8, 129.7, 128.5, 128.4, 96.5 (d, 184 Hz, C-2), 79.0 (d, 29 Hz, C-3), 65.2 (d, 4 Hz, C-5), 48.5 (C-4), 34.9 (d, 23 Hz, C-1).

1,4-Anhydro-2-deoxy-2-fluoro-3,5-di-O-benzoyl-4-sulphinyl-D-arabinitol (C10)

114.53 g (206.35 mmol assuming a yield of 100% in step C9) of C9 (crude product) are dissolved in 400 ml of acetone, and 60 ml of water are added. At 20° C., 69.77 g (113.49 mmol) of OXONE are then added a little at a time. The reaction is checked for complete conversion, and a dilute solution of sodium sulphite is then added. The reaction mixture is neutralized using saturated sodium bicarbonate solution, and the acetone is then removed completely by distillation under reduced pressure. Dichloromethane is added to the suspension, the solid is filtered off and the filtercake is washed product-free with dichloromethane. The solution of the crude product is redistilled to MTBE and isolated in this solvent. This gives 56.4 g (72.6% over three steps with C7) of C10.

$^1$H-NMR (400 MHz, CDCl$_3$): 8.05 (m, 4H), 7.60 (m, 2H), 7.45 (m, 4H), 5.83 (m, 1H), 5.74 (m, 1H), 4.89 (ddd, 1H, 12.1 Hz, 5.1 Hz, 0.9 Hz), 4.75 (ddd, 1H, 12.4 Hz, 7.6 Hz, 0.9 Hz), 3.65 (m, 1H), 3.75 (m, 1H), 3.45 (m, 1H).

$^{13}$C-NMR (75 MHz, CDCl$_3$): 165.7, 165.2 (C=O), 134.0, 133.5, 130.0, 129.7, 128.6, 128.5 (Ar), 95.4 (d, 185 Hz, C-2), 77.2 (d, 33 Hz, C-3), 71.6 (C-4), 61.1 (d, 2 Hz, C-5), 55.8 (d, 19 Hz, C-1).

1-O-Acetyl-2-deoxy-2-fluoro-3,5-di-O-benzoyl-4-thio-β-D-arabinofuranose (IIβ)

80 ml of acetic anhydride and 361 mg (2.66 mmol) of potassium bisulphate are added to 10 g (26.57 mmol) of C10, and the mixture is stirred at 80° C. until the reaction is ended. The reaction mixture is then codistilled initially repeatedly with toluene and then with ethanol. Finally, the product is crystallized from ethanol. This gives 8.9 g (80%) of the compound IIβ.

$^1$H-NMR (400 MHz, CDCl$_3$): 8.10-7.90 (m, 4H, Ar), 7.63-7.29 (m, 6H, Ar), 6.18 (d, 1H, 4.4 Hz), 6.12-6.02 (m, 1H), 5.45 (dd, 1H, 9.04 Hz, 4.52 Hz), 5.28 (dd, 1H, 8.85 Hz, 4.52 Hz), 4.68 (dd, 1H, 11.49 Hz, 6.22 Hz), 4.49 (dd, 1H, 11.49 Hz, 6.41 Hz), 3.74 (dd, 1H, 13.56 Hz, 6.40 Hz), 2.12 (s, 3H).

$^{13}$C-NMR (75 MHz, CDCl$_3$): 169.6 (COCH$_3$), 165.8, 165.4 (COPh), 133.6, 133.1 (Ar) 129.8, 129.7, 128.5, 128.2 (Ar), 92.5 (d, 207 Hz, C-2), 75.7 (d, 23 Hz, C-3), 74.0 (d, 17 Hz, C-1), 66.1 (C-5), 42.4 (d, 7 Hz, C-4), 21.0 (CH$_3$).

Melting point: 130° C.

The process of the present invention provides an industrially advantageous and excellent preparation of the compounds of the formula I.

The invention claimed is:
1. A process for preparing a compound of formula I

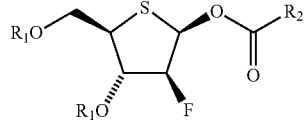

wherein

R₁ represents —C(O)—C₁-C₆-alkyl or —C(O)-aryl; and

R₂ represents C₁-C₆-alkyl, C₁-C₄-perfluoroalkyl or aryl, which comprises the following steps:

(1) reduction of a lyxonolactone of formula IV

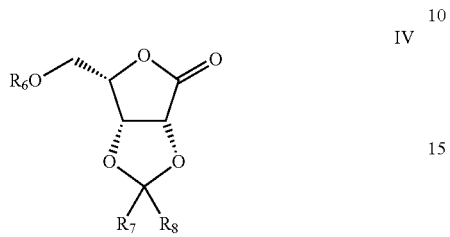

wherein

R₆ represents C₁-C₆-alkyl or arylmethylene; and

R₇ and R₈ independently represent hydrogen, C₁-C₆-alkyl, C₁-C₄-perfluoroalkyl or aryl;

in the presence of 0.5-10 molar equivalents of hydride donors of the formula A(AlH₄) or A(BH₄), wherein A is an alkali metal, to give a diol of formula V:

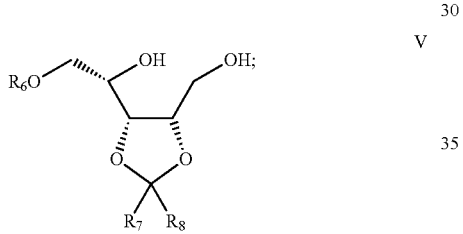

(2) reaction of the diol of formula V with at least 2 molar equivalents of sulphonyl chloride R₉—SO₂Cl or sulphonic anhydride R₉—SO₂—O—SO₂—R₉, wherein R₉ represents C₁-C₆-alkyl, C₁-C₄-perfluoroalkyl or aryl, in the presence of at least 2 molar equivalents of a tertiary amine or a pyridine, to give a compound of formula VI:

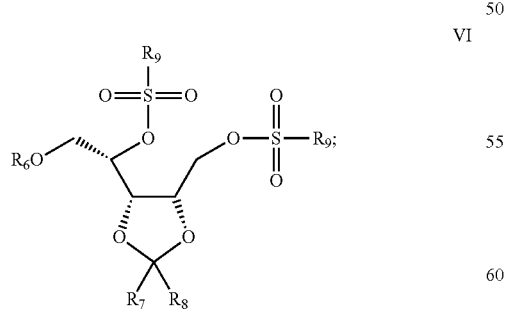

(3) reaction of the bissulphonate of formula VI with at least 1 molar equivalent of sodium sulphide (Na₂S) in a polar aprotic solvent, at a temperature of more than 50° C., to give a thiofuranose of formula VII:

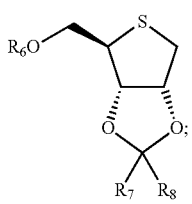

(4) conversion of the thiofuranose of formula VII in a solvent mixture of water and an organic solvent selected from the group of ethers, alcohols, and aromatic hydrocarbons, with 0.01-5 molar equivalents of an acid selected from the group of mineral acids, alkanesulphonic acids, arylsulphonic acids, perfluorosulphonic acids and perfluoroalkanecarboxylic acids, into a diol of formula VIII:

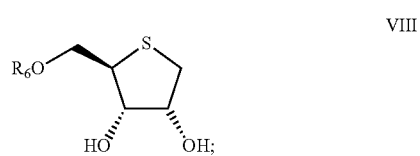

(5) reaction of the diol of formula VIII in the presence of at least 0.2 molar equivalents of a base of the formula AH, A₂CO₃ or A(OtBu), wherein A represents an alkali metal; with 1-2 molar equivalents of a diol-activating reagent of the formula X₁—SO₂—X₂, wherein X₁ and X₂ independently represent Cl or imidazoyl, to give a cyclic sulphate ester of formula IX:

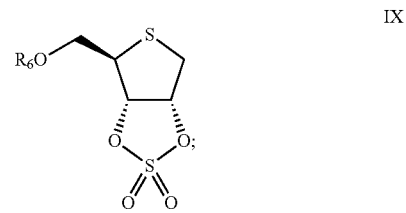

(6) the cyclic sulphate ester of formula IX is initially reacted with 1-3 molar equivalents of an ammonium fluoride of the formula N(R₁₁)₄F, wherein R₁₁ represents C₁-C₆-alkyl, at a temperature between 0° C. and 30° C., and the reaction mixture obtained in this manner is reacted with an acid selected from the group of mineral acids, alkylsulphonic acids, arylsulphonic acids, perfluorosulphonic acids and perfluoroalkanecarboxylic acids to give an ether of formula X:

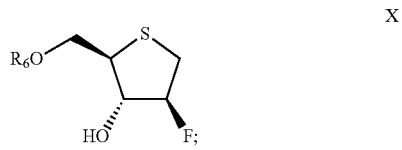

(7) the ether of formula X is in partial step a) reacted in the presence of at least 1 molar equivalent of a boron halide BY₃, wherein Y represents F, Cl or Br, at a temperature between 0° C. and −80° C.;

in partial step b), the reaction mixture obtained in partial step a) is reacted with a mixture of an alcohol component selected from the group consisting of $C_1$-$C_6$-alkanol, aryl alkanol and phenols; and a base selected from the group of aliphatic tertiary amines and pyridines; to give a diol of formula XI:

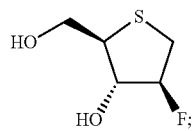

XI (8) the diol of formula XI is in the presence of at least 2 molar equivalents of a base selected from the group of aliphatic tertiary amines and pyridines, reacted with at least 2 molar equivalents of an acid chloride $R_1$—Cl or an acid anhydride $R_1$—O—$R_1$, wherein $R_1$ represents —C(O)—$C_1$-$C_6$-alkyl or —C(O)-aryl; to give a compound of formula XII:

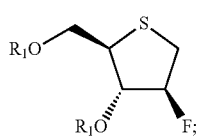

XII (9) the sulphide of formula XII is oxidized in a solvent mixture of water and a ketone of the formula $R_9$—C(O)—$R_9'$, wherein $R_9$ and $R_9'$ independently represents $C_1$-$C_6$-alkyl, $C_1$-$C_4$-perfluoroalkyl or aryl, with 0.5-1 molar equivalent of an alkali metal persulphate of the formula $AHSO_5$, wherein $A^+$ represents an alkali metal, at a temperature between 0° C. and 50° C. to give a sulphoxide of formula XIII:

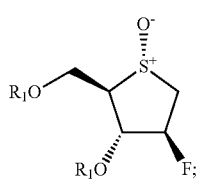

XIII

(10) the sulphoxide of formula XIII is reacted with at least 1 molar equivalent of an acid anhydride $R_2$—C(O)—O—C(O)—$R_2$, wherein $R_2$ represents $C_1$-$C_6$-alkyl, $C_1$-$C_4$-perfluoroalkyl or aryl; in the presence of 0.01-2 molar equivalents of a protic acid selected from mineral acids, alkanesulphonic acids, arylsulphonic acids, perfluorosulphonic acids and perfluoroalkanecarboxylic acids, or
in the presence of 0.01-2 molar equivalents of a Lewis acid selected from LiCl, $MgBr_2$ and $Ti(OR_{13})_4$, wherein $R_{13}$ represents $C_1$-$C_6$-alkyl or arylmethylene; at a temperature between 30° C. and 100° C.

2. The process according to claim 1 for preparing a compound of formula I wherein
$R_1$ represents benzoyl, and
$R_2$ represents methyl.

3. The process according to claim 2 for preparing a compound of formula IIβ

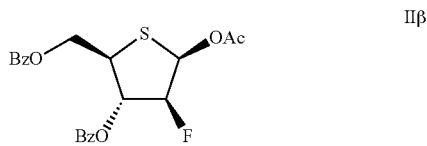

IIβ wherein
$R_7$, $R_8$ and $R_9$ represent methyl, and
$R_6$ represents benzyl.

4. The process according to claim 1, wherein in step (1) 0.5-1.5 molar equivalents of lithium aluminium hydride (LiAlH$_4$) are used.

5. The process according to claim 1, wherein the step (1) and/or the step (2) are carried out at a temperature between 0° C. and 30° C.

6. The process according to claim 1, wherein in step (2) 2-5 molar equivalents of methanesulphonyl chloride and 2-5 molar equivalents of triethylamine are used.

7. The process according to claim 1, wherein the reaction in step (3) is carried out at a temperature between 50° C. and 100° C. in N-methylpyrrolidone.

8. The process according to claim 1, wherein the reaction in step (4) is carried out in a mixture of tetrahydrofuran (THF) and water with 0.01-5 molar equivalents of $H_2SO_4$ at a temperature between 20° C. and 100° C.

9. The process according to claim 1, wherein in step (4) the isolation of the diol VIII is carried out by crystallization from a solvent mixture of heptane and isopropyl acetate or ethyl acetate.

10. The process according to claim 1, wherein in step (5) 0.2-3 molar equivalents of sodium hydride and 1-2 molar equivalents of sulphonyldiimidazole are used at a temperature between -5° C. and 20° C.

11. The process according to claim 1, wherein in step (6) 1-3 molar equivalents of tetrabutylammonium fluoride are used.

12. The process according to claim 1, wherein in step (6) the reaction mixture obtained in the first partial step is reacted at a temperature between 20° C. and 70° C. with sulphuric acid ($H_2SO_4$).

13. The process according to claim 1, wherein in partial step a) of step (7) 1-4 molar equivalents of boron trichloride are used.

14. The process according to claim 1, wherein in partial step b) of step (7) the reaction mixture of methanol and pyridine obtained in partial step a) is reacted.

15. The process according to claim 1, wherein the partial steps of step (7) are carried out at temperatures between 0° C. and -80° C.

16. The process according to claim 1, wherein step (8) is carried out in the presence of 2-10 molar equivalents of pyridine using 2-5 molar equivalents of benzoyl chloride.

17. The process according to claim 1, wherein step (9) is carried out in a solvent mixture of water and acetone using 0.5-1 molar equivalent of OXONE.

18. The process according to claim 1, wherein in step (9) the sulphoxide XIII is isolated by crystallization from methyl tert-butyl ether.

19. The process according to claim 1, wherein step (10) is carried out in the presence of 0.01-2 molar equivalents of potassium bisulphate using at least 5 molar equivalents of acetic anhydride.

20. The process according to claim 1, wherein in step (10) the product I is isolated by crystallization from ethanol.

21. A process for preparing a compound of formula I:

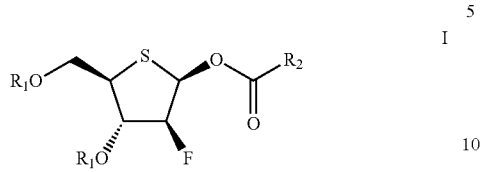

wherein
R$_1$ represents —C(O)—C$_1$-C$_6$-alkyl or —C(O)-aryl; and
R$_2$ represents C$_1$-C$_6$-alkyl, C$_1$-C$_4$-perfluoroalkyl or aryl, which comprises reacting a sulphoxide of formula XIII:

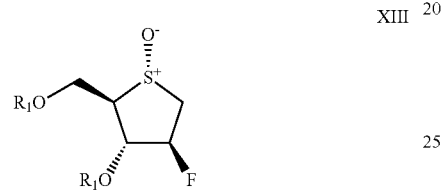

wherein R$_1$ represents benzoyl, at a temperature between 30° C. and 100° C. with at least 1 molar equivalent of an acid anhydride R$_2$—C(O)—O—C(O)—R$_2$, wherein R$_2$ represents C$_1$-C$_6$-alkyl, C$_1$-C$_4$-perfluoroalkyl or aryl; in the presence of 0.01-2 molar equivalents of a protic acid selected from the group of mineral acids, alkanesulphonic acids, arylsulphonic acids, perfluorosulphonic acids and perfluoroalkanecarboxylic acids, or in the presence of 0.01-2 molar equivalents of a Lewis acid, wherein R$_{13}$ represents C$_1$-C$_6$-alkyl or arylmethylene.

22. The process according to claim 21, wherein the reaction is carried out in the presence of 0.01-2 molar equivalents of potassium bisulphate using at least 5 molar equivalents of acetic anhydride.

23. The process according to claim 21, wherein the product IIβ is isolated by crystallization from ethanol.

24. A process for preparing a compound of formula X

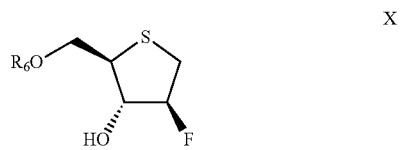

wherein R$_6$ represents C$_1$-C$_6$-alkyl, arylmethylene, which comprises the following steps:
(a) a cyclic sulphate ester of formula IX

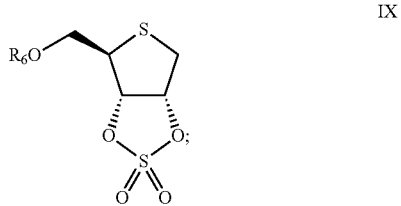

is initially reacted with 1-3 molar equivalents of an ammonium fluoride of the formula N(R$_{11}$)$_4$F, wherein R$_{11}$ represents C$_1$-C$_6$-alkyl, at a temperature between 0° C. and 30° C., and
(b) the reaction mixture obtained in this manner is reacted with an acid selected from the group of mineral acids, alkylsulphonic acids, arylsulphonic acids, perfluorosulphonic acids and perfluoroalkanecarboxylic acids.

25. The process according to claim 24, wherein 1-3 molar equivalents of tetrabutylammonium fluoride are used.

26. The process according to claim 24, wherein the reaction mixture obtained in the first partial step is reacted at a temperature between 20° C. and 70° C. with sulphuric acid (H$_2$SO$_4$).

* * * * *